(12) United States Patent
Benedict et al.

(10) Patent No.: US 10,524,775 B2
(45) Date of Patent: *Jan. 7, 2020

(54) METHODS OF REPAIRING CARTILAGE DEFECTS

(71) Applicant: ARTHREX, INC., Naples, FL (US)

(72) Inventors: Robert Benedict, Fort Myers, FL (US); Marc Stoll, Fort Myers, FL (US); James L. Cook, Columbia, MO (US)

(73) Assignee: ARTHREX, INC., Naples, FL (US)

( * ) Notice: Subject to any disclaimer, the term of this patent is extended or adjusted under 35 U.S.C. 154(b) by 336 days.

This patent is subject to a terminal disclaimer.

(21) Appl. No.: 14/790,570

(22) Filed: Jul. 2, 2015

(65) Prior Publication Data

US 2017/0000473 A1  Jan. 5, 2017

(51) Int. Cl.
*A61B 17/04* (2006.01)
*A61F 2/30* (2006.01)

(52) U.S. Cl.
CPC .. *A61B 17/0401* (2013.01); *A61B 2017/0404* (2013.01); *A61B 2017/044* (2013.01); *A61F 2002/30751* (2013.01); *A61F 2002/30766* (2013.01)

(58) Field of Classification Search
CPC ........ A61F 2/30756; A61F 2002/30751; A61F 2002/30766; A61B 17/0401
See application file for complete search history.

(56) References Cited

U.S. PATENT DOCUMENTS

| 3,318,774 | A | * | 5/1967 | Dingwall | A01N 1/0205 424/548 |
|---|---|---|---|---|---|
| 4,772,286 | A | * | 9/1988 | Goble | A61B 17/686 606/66 |
| 4,773,910 | A | * | 9/1988 | Chen | A61F 2/08 623/13.2 |
| 5,139,520 | A | * | 8/1992 | Rosenberg | A61B 17/1675 606/102 |
| 5,713,374 | A | | 2/1998 | Pachence et al. | |
| 5,964,764 | A | * | 10/1999 | West, Jr. | A61F 2/0805 606/232 |
| 6,440,141 | B1 | | 8/2002 | Philippon | |
| 6,488,033 | B1 | | 12/2002 | Cerundolo | |
| 7,326,222 | B2 | * | 2/2008 | Dreyfuss | A61B 17/0469 606/103 |
| 7,361,195 | B2 | | 4/2008 | Schwartz et al. | |
| 7,371,260 | B2 | | 5/2008 | Malinin | |
| 7,488,347 | B1 | * | 2/2009 | Goble | A61F 2/30749 623/18.11 |
| 7,641,694 | B1 | | 1/2010 | Goble et al. | |

(Continued)

OTHER PUBLICATIONS

International Preliminary Report on Patentability for International application No. PCT/US2015/059192 dated Oct. 12, 2017.

(Continued)

*Primary Examiner* — Bruce E Snow
*Assistant Examiner* — Melissa A Hoban
(74) *Attorney, Agent, or Firm* — Carlson, Gaskey & Olds

(57) ABSTRACT

A method for repairing a cartilage defect according to an exemplary aspect of the present disclosure includes, among other things, preparing a cartilage defect for implantation of a cartilage graft and attaching the cartilage graft via a transosseus tunnel.

20 Claims, 4 Drawing Sheets

(56) References Cited

U.S. PATENT DOCUMENTS

| | | | |
|---|---|---|---|
| 7,666,230 B2 | 2/2010 | Orban et al. | |
| 7,749,250 B2 * | 7/2010 | Stone | A61B 17/0401 606/232 |
| 7,901,461 B2 | 3/2011 | Harmon et al. | |
| 7,931,695 B2 | 4/2011 | Ringeisen | |
| 8,012,205 B2 | 9/2011 | Plouhar et al. | |
| 8,016,867 B2 | 9/2011 | Bowman | |
| 8,062,654 B2 * | 11/2011 | Nelson | A61K 47/6953 424/426 |
| 8,142,502 B2 | 3/2012 | Stone et al. | |
| 8,444,968 B2 | 5/2013 | Seyedin et al. | |
| 8,449,561 B2 | 5/2013 | Bowman | |
| 8,518,433 B2 | 8/2013 | Kizer et al. | |
| 8,524,268 B2 | 9/2013 | Kizer et al. | |
| 8,535,703 B2 | 9/2013 | Schmieding et al. | |
| 8,545,535 B2 * | 10/2013 | Hirotsuka | A61B 17/0401 606/232 |
| 8,597,352 B2 | 12/2013 | Schwartz | |
| 8,637,066 B2 | 1/2014 | Binnette et al. | |
| 8,641,775 B2 | 2/2014 | Harmon et al. | |
| 8,657,881 B2 | 2/2014 | Kladakis et al. | |
| 8,734,828 B2 * | 5/2014 | Kaps | A61L 27/48 424/423 |
| 8,834,568 B2 | 9/2014 | Shapior | |
| 8,834,914 B2 | 9/2014 | Kizer et al. | |
| 8,882,774 B2 | 11/2014 | Malinin | |
| 8,895,045 B2 | 11/2014 | Jamiolkowski et al. | |
| 9,066,716 B2 * | 6/2015 | Sikora | A61B 17/0401 |
| 9,855,146 B2 * | 1/2018 | Schmieding | A61F 2/30756 |
| 2005/0149118 A1 | 7/2005 | Koyfman et al. | |
| 2006/0293710 A1 | 12/2006 | Foerster et al. | |
| 2007/0135843 A1 | 6/2007 | Burkhart | |
| 2007/0288023 A1 | 12/2007 | Pellegrino et al. | |
| 2008/0039954 A1 * | 2/2008 | Long | A61F 2/30756 623/23.76 |
| 2008/0125863 A1 * | 5/2008 | McKay | A61F 2/30756 623/11.11 |
| 2008/0195205 A1 * | 8/2008 | Schwartz | A61B 17/0642 623/14.12 |
| 2008/0255613 A1 | 10/2008 | Kaiser et al. | |
| 2008/0269674 A1 * | 10/2008 | Stone | A61B 17/1635 604/80 |
| 2009/0024229 A1 | 1/2009 | Chen et al. | |
| 2009/0312842 A1 | 12/2009 | Bursac et al. | |
| 2010/0016892 A1 | 1/2010 | Kaiser et al. | |
| 2010/0040662 A1 | 2/2010 | Cotton et al. | |
| 2010/0168869 A1 | 7/2010 | Long et al. | |
| 2011/0091517 A1 | 4/2011 | Binette et al. | |
| 2011/0245929 A1 | 10/2011 | Rakin et al. | |
| 2012/0207718 A1 | 8/2012 | Stone et al. | |
| 2013/0138123 A1 * | 5/2013 | Stone | A61B 17/0401 606/148 |
| 2013/0158601 A1 * | 6/2013 | Stone | A61B 17/0401 606/232 |
| 2013/0338792 A1 | 12/2013 | Schmieding et al. | |
| 2014/0017283 A1 | 1/2014 | Yoo et al. | |
| 2014/0031863 A1 * | 1/2014 | Gittings | A61B 17/0401 606/232 |
| 2014/0142718 A1 | 5/2014 | Seyedin et al. | |
| 2014/0222162 A1 | 8/2014 | Seedhom | |
| 2015/0057750 A1 * | 2/2015 | Timmerman | A61B 17/0401 623/13.14 |
| 2015/0182233 A1 | 7/2015 | Van Wyk et al. | |
| 2016/0287243 A1 * | 10/2016 | Benedict | A61B 17/0401 |

OTHER PUBLICATIONS

International Search Report and Written Opinion of the International Searching Authority for International application No. PCT/US2015/059192 dated Feb. 3, 2016.

Streit, Jomnathan J., et al., Fresh osteochondral allograft for shoulder resurfacing relieves pain, Orthopedics Today, Oct. 2013, https://www.healio.com/orthopedics/shoulder-elbow/news/print/orthopedics-today/%7bccb . . . , printed Mar. 22, 2018.

* cited by examiner

METHODS OF REPAIRING CARTILAGE DEFECTS

BACKGROUND

This disclosure relates to a surgical method for fixating a cartilage graft to bone to repair a cartilage defect.

SUMMARY

Disclosed herein are methods regarding repairing a cartilage defect. For example, method(s) as described herein include, inter alia, preparing a cartilage defect for implantation of a cartilage graft and attaching the cartilage graft to bone. The cartilage graft can be attached to a bone via a fixation device(s). A fixation device can include, but is not limited to, a button, an anchor, a screw, a suture construct (e.g., a bone bridge). A suture constructed can be either knotted or knotless. Methods can further include creating one or more transosseus tunnels.

In an embodiment, a method of repairing a cartilage defect includes creating at least one transosseus tunnel; attaching a flexible strand to a cartilage graft; transiting the cartilage graft through the at least one transosseus tunnel; and fixating the cartilage graft to bone.

In a further non-limiting embodiment of the foregoing method, the preparing step includes creating vertical margins around a periphery of the cartilage defect.

In a further non-limiting embodiment of either of the foregoing methods, the preparing step includes removing at least a portion of the cartilage defect. In an illustrative embodiment, a portion of the cartilage can be removed with a curette.

In a further non-limiting embodiment of any of the foregoing methods, the preparing step includes performing bone marrow stimulation to the cartilage defect.

In a further non-limiting embodiment of any of the foregoing methods, the step of performing the bone marrow stimulation includes performing a microfracture procedure.

In a further non-limiting embodiment of any of the foregoing methods, the preparing step includes drying the cartilage defect.

In a further non-limiting embodiment of any of the foregoing methods, the attaching step includes passing a flexible strand through the cartilage graft, loading a free end of the flexible strand through a portion of the at least one fixation device, tensioning the flexible strand to approximate the cartilage graft to the bone and inserting the fixation device into the bone to fixate the cartilage graft to the bone.

In a further non-limiting embodiment of any of the foregoing methods, the inserting step includes moving fixation device toward the portion inside the bone to trap the flexible strand between the bone and the fixation device.

In a further non-limiting embodiment of any of the foregoing methods, the attaching step includes implanting at least one fixation device into the bone, passing a flexible strand of the at least one fixation device through the cartilage graft and tensioning the flexible strand to approximate the cartilage graft to the bone.

In a further non-limiting embodiment of any of the foregoing methods, the tensioning step includes shuttling a free end of the flexible strand through the flexible strand to create a spliced loop around the cartilage graft.

In a further non-limiting embodiment of any of the foregoing methods, the at least one fixation device includes a first knotless suture anchor and a second knotless suture anchor. The attaching step includes implanting the first knotless suture anchor into the bone, passing a flexible strand connected to the first knotless suture anchor through the cartilage graft and tensioning the flexible strand to approximate the cartilage graft to the bone.

In a further non-limiting embodiment of any of the foregoing methods, the attaching step includes passing a second flexible strand through the cartilage graft, loading the second flexible strand through a portion of the fixation device, tensioning the second flexible strand and inserting the fixation device into bone.

In a further non-limiting embodiment of any of the foregoing methods, at least one fixation device is a soft knotless anchor assembly.

In a further non-limiting embodiment of any of the foregoing methods, at least one knotless suture anchor includes an eyelet.

In a further non-limiting embodiment of any of the foregoing methods, at least one knotless suture anchor and the second knotless suture anchor includes a shuttle device configured to shuttle the flexible strand.

A method for repairing a cartilage defect according to another exemplary aspect of the present disclosure includes, among other things, passing a flexible strand through a cartilage graft, tensioning the flexible strand to approximate the cartilage graft relative to bone associated with the cartilage defect and inserting a knotless suture anchor into the bone to knotlessly fixate the cartilage graft to the bone.

In a further non-limiting embodiment of the foregoing method, the method includes creating a pilot hole in the bone prior to the step of inserting the knotless suture anchor.

In a further non-limiting embodiment of either of the foregoing methods, the tensioning step occurs before the inserting step.

In a further non-limiting embodiment of any of the foregoing methods, the tensioning step occurs after the inserting step.

In a further non-limiting embodiment of any of the foregoing methods, the method includes loading a free end of the flexible strand through a portion of the knotless suture anchor.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure describes surgical methods for repairing cartilage defects. The surgical methods include attaching a cartilage graft to bone using at least one fixation device. In some embodiments, the fixation device is implanted into bone before tensioning a flexible strand, such as a suture, to approximate the cartilage graft to the bone. In other embodiments, the fixation device is implanted into bone after tensioning the flexible strand to approximate the cartilage graft to the bone. These and other features are described in greater detail in the following paragraphs of this detailed description.

Repetitive trauma to a joint, such as a knee, ankle, hip, or shoulder joint, may cause cartilage defects. Cartilage defects include localized areas of damaged articular cartilage and, potentially, adjacent subchondral bone. Cartilage defects typically do not heal without treatment. If not treated, a defect can deteriorate articulate cartilage and/or underlying bone of the joint, thereby causing relatively significant arthritic pain.

FIGS. 1-6 schematically illustrate methods of repairing a cartilage defect 10 located within a joint 12. The methods are illustrated and described as an arthroscopic method; however, methods could alternatively be performed as an open procedure. The cartilage defect 10 can include osteochondral and/or chondral defects. In other words, a cartilage defect 10 may include localized areas of damaged articular cartridge and/or damaged subchondral bone of the joint 12. In one embodiment, the joint 12 is a knee joint. However, methods of this disclosure may be used to repair cartilage defects located anywhere within the human body, including but not limited to, knee, talus, elbow, shoulder, hip, and temporomandibular joints.

Figure 1:
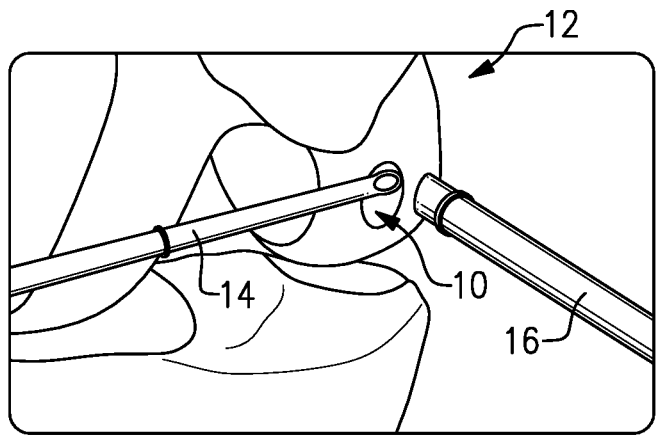
FIGS. 1 and 2 schematically illustrate preparing a cartilage defect for implantation of a cartilage graft.
Figure 3:
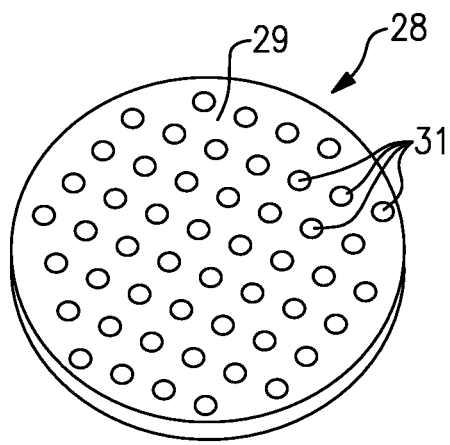
FIG. 3 illustrates an exemplary cartilage graft.

An exemplary repair method begins by prepping the cartilage defect 10 for receiving a cartilage graft 28 (shown in FIG. 3). Referring first to FIG. 1, after a surgeon has identified a cartilage defect 10 within a joint 12, the cartilage defect 10 may be debrided to a stable border having perpendicular margins. Tools, such as a curette 14 and an elevator 16, can be used to create vertical margins around a periphery of the cartilage defect 10.

Figure 2:
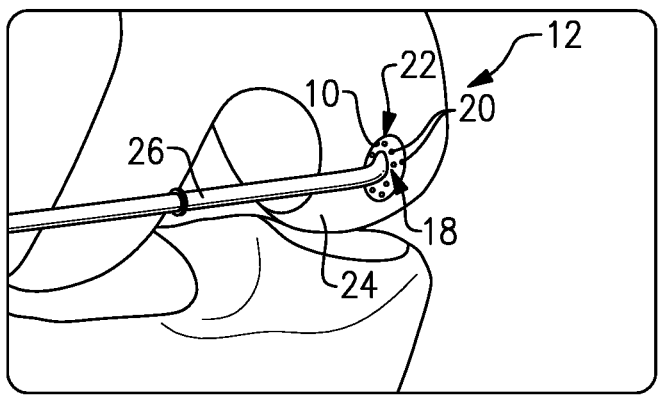

A cartilage defect 10 may be prepped with our without bone marrow stimulation. In an embodiment, a cartilage defect 10 is further prepared by performing bone marrow stimulation. For example, as shown in FIG. 2, a microfracture procedure or some other technique may optionally be performed to obtain a bleeding bone bed 18. During microfracture surgery, multiple perforations 20 are created in subchondral bone 22 that extends beneath articular cartilage 24 associated with a cartilage defect 10. A bleeding bone bed 18 may be created using a tool 26, such as Arthrex's Powerpick™, to create perforations 20. Formation of perforations 20 creates a bleeding bone bed 18, which stimulates bone marrow seepage at the repair site. Other techniques can also be used to create a bleeding bone bed 18, including but not limited to, drilling, hammering, curetting, scraping, etc.

A cartilage defect 10 may also be dried to complete surgical preparation of the cartilage defect 10. A cartilage defect 10 may be dried to remove excess moisture that could interfere with implantation of a cartilage graft 28. The cartilage defect 10 may be dried using any known technique.

In an illustrative embodiment, at least one transosseus tunnel (e.g., 1, 2, 3, 4, or 5) can be created in one or more bones adjacent a cartilage defect. In an embodiment, a transosseus tunnel can be created by drilling (e.g., an Arthrex Flipcutter®). In an embodiment, a transosseus tunnel can be created in the tibia, femur, calcaneus, humerus, acetabulum, mandible, temporal bone, or phalanges. In an illustrative embodiment, one or more transosseus tunnels can exit in a cartilage defect.

A cartilage graft 28 may be implanted after adequately prepping a cartilage defect 10. A cartilage graft 28 serves as a scaffold over a cartilage defect 10, thereby providing a tissue network that can potentially signal autologous cellular interactions. The size and shape of a cartilage graft 28 may be selected using a template that is placed over the cartilage defect 10 and marked to indicate its general size. A template may then be used to trim a cartilage graft 28 down to the desired size and shape.

One exemplary cartilage graft 28 is illustrated in FIG. 3. In one non-limiting embodiment, a cartilage graft 28 includes a cartilage disk 29 having a plurality of pores 31 formed through the cartilage disk 29. The cartilage graft 28 may be made of human tissue (e.g., allograft cartilage), synthetic materials, xeno materials, etc. In one non-limiting embodiment, a cartilage graft 28 is made of a micronized cartilage matrix. Although shown as being porous, a cartilage graft 28 is not limited to such an embodiment.

Figure 4A:
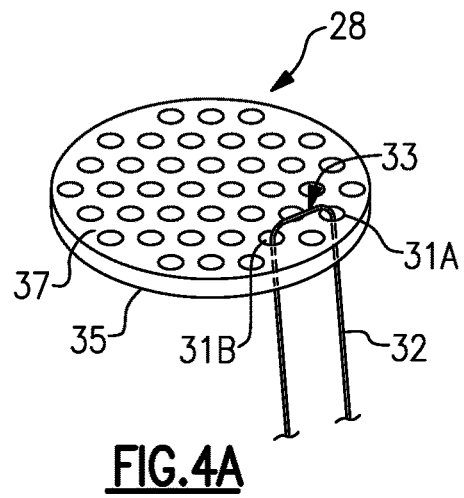
FIGS. 4A, 4B, 4C and 4D schematically illustrate knotlessly fixating a cartilage graft to bone.

As shown in FIG. 4A, a flexible strand 32, such as a suture, can be passed through a cartilage graft 28. A mattress stitch 33 may be formed to connect the flexible strand 32 to the cartilage graft 28. A mattress stitch 33 is formed by inserting a flexible strand 32 through a pore 31A in a direction from the bottom 35 toward a top 37 of the disk 29 of the cartilage graft 28 and then inserting the flexible strand 32 through an adjacent pore 31B in a direction from the top 37 toward the bottom 35 of the disk 29. Other suturing techniques and configurations are also contemplated within the scope of this disclosure. For example, in situations where the cartilage graft 28 is not porous, the flexible strand 32 may be simply threaded through the cartilage graft 28.

Figure 4B:
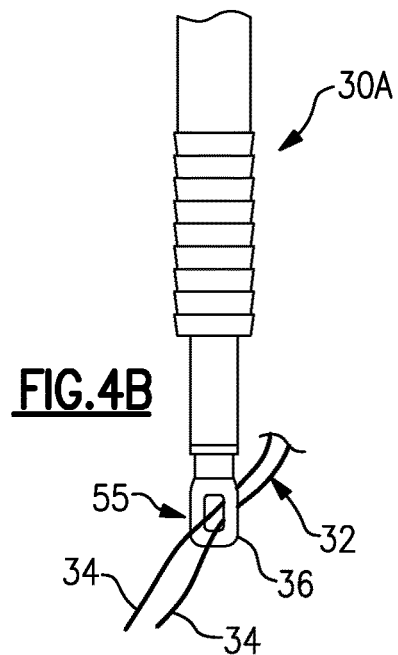
Figure 4C:
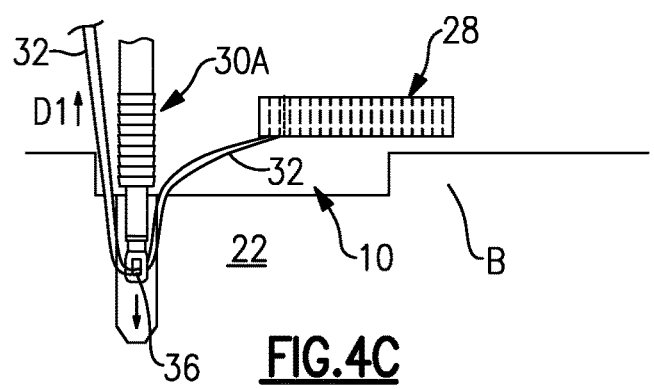
Figure 4D:
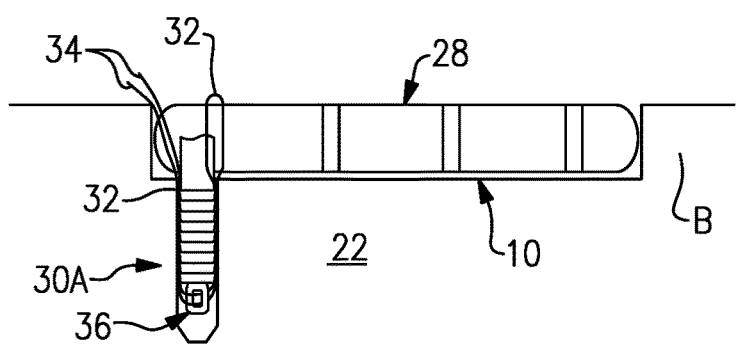

Next, as shown in FIG. 4B, one or more free ends 34 of a flexible strand 32 are loaded through a portion 55 of a knotless suture anchor 30A. In one non-limiting embodiment, the portion 55 includes an eyelet 36 of the knotless suture anchor 30A.

Knotless techniques are considered "knotless" because there is no need to tie knots in a flexible strand 32 in order to secure a cartilage graft 28 to bone.

Multiple different fixation patterns may be used to secure the cartilage graft 28 to the bone B. For example, the cartilage graft 28 can be fixated by positioning flexible strands 32 at each of its four quadrants (see FIG. 6A), through its center and about its periphery (see FIG. 6B), through its top and bottom halves (see FIG. 6C), or at each third of the cartilage graft 28 (see FIG. 6D). Other fixation patterns could also be used.

In another embodiment, a layer of fibrin may be applied over a cartilage graft 28 after it has been fixated to bone. Fibrin may be applied using an applicator. After the fibrin and the cartilage graft sit for a predefined amount of time, such as approximately five minutes, the joint 12 may be gently ranged before closure to assure adherence of the fibrin 50 and the cartilage graft 28 to the bone B.

In an illustrative embodiment, a flexible strand can be passed through a cartilage graft and pulling the graft through the transosseus tunnel. Once through the transosseus tunnel, the flexible strand can be tensioned to approximate the cartilage graft to the bone. Once approximated, the cartilage graft can be fixated to the bone via one or more fixation devices. A fixation device can be an anchor, a screw, a button, or a suture construct.

Figure 5:
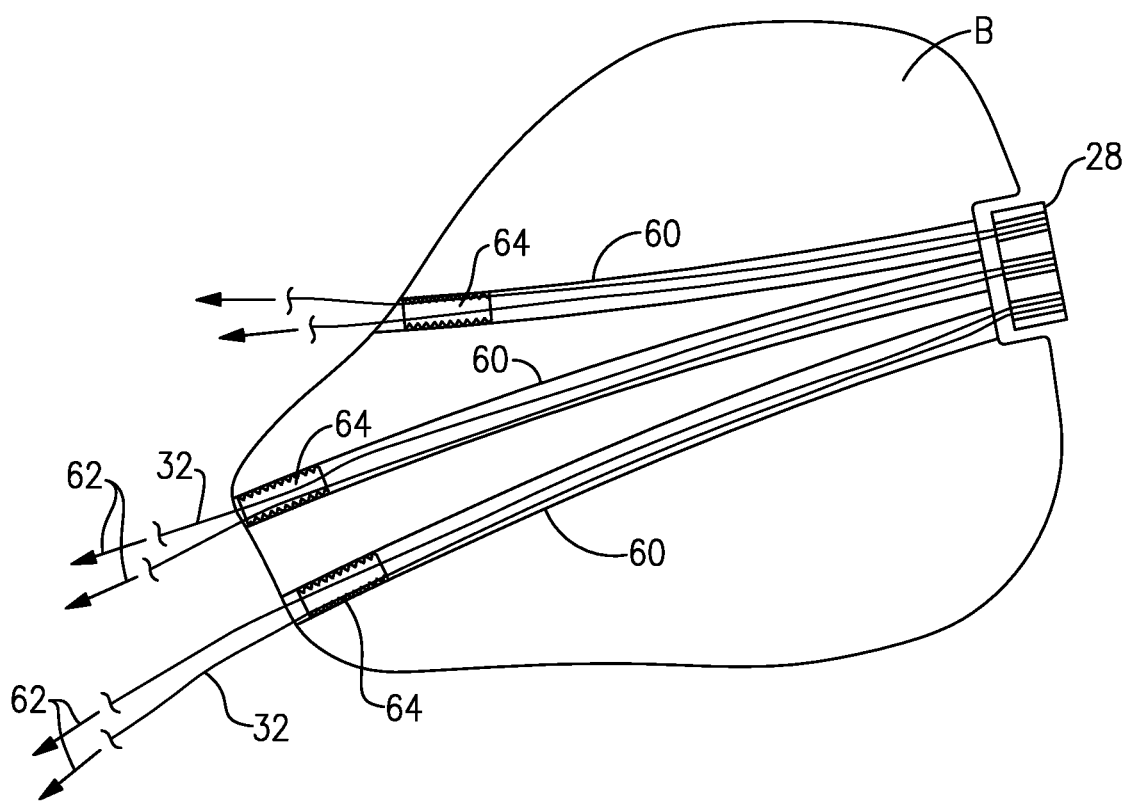
FIG. 5 schematically illustrates repairing a cartilage defect.
Figure 6A:
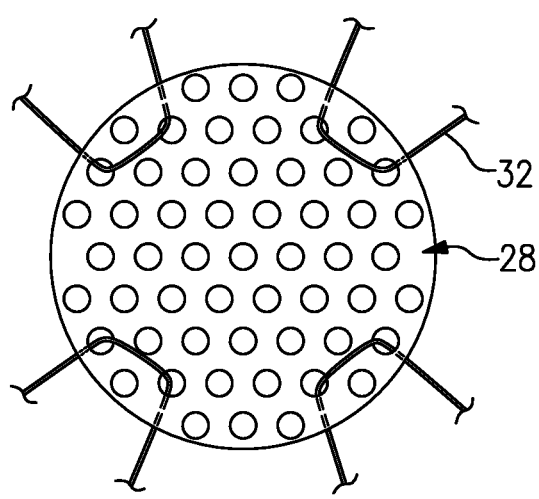
FIGS. 6A, 6B, 6C and 6D illustrate exemplary fixation patterns for fixating a cartilage graft to a bone.
Figure 6B:
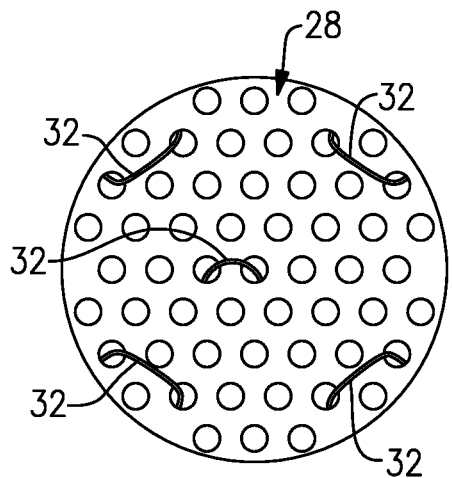
Figure 6C:
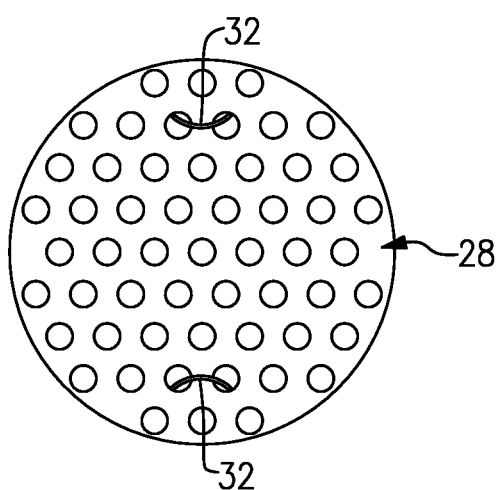
Figure 6D:
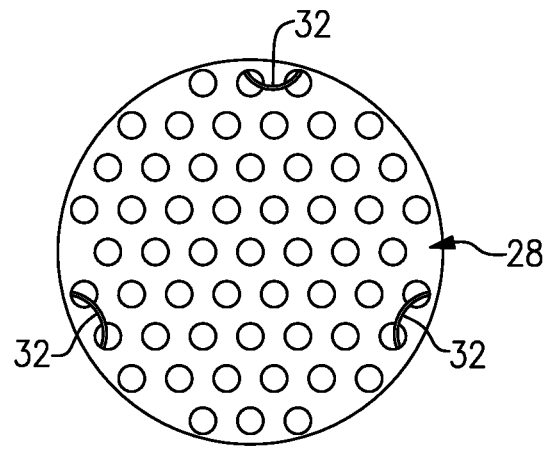

In an illustrative embodiment, shown in FIG. 5, a method for repairing a cartilage defect includes drilling at least one transosseus tunnel 60; tensioning a flexible strand 32 that is passed through a cartilage graft 28 through at least one transosseus tunnel 60; and fixating the cartilage graft 28 to bone B. In an embodiment, a flexible strand 32 is tensioned (schematically shown by arrows 62) through more than one transosseus tunnels 60 (three shown in FIG. 5). In an illustrative embodiment, a cartilage graft 28 can be fixated to bone B via a fixation device 64, which can be a button, a screw, an anchor, or a suture construct. An embodiment includes a method comprising more than one fixation device 64, which can be a button, a screw, an anchor, a suture construct, or combinations thereof. A suture construct can be knotted or knotless. A suture construct can be a pattern of suture that secures the graft to a bone (e.g., SutureBridge®, SpeedBridge™, etc.).

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method for repairing a cartilage defect, comprising:
   a) performing a bone marrow stimulation at the cartilage defect, wherein the bone marrow stimulation comprises a microfracture procedure;
   b) drilling at least one transosseus tunnel, wherein the at least one transosseus tunnel extends continuously from a first opening at a first location of a bone to a second opening at a second location of the bone;
   c) passing a flexible strand through at least two different openings of a cartilage graft, wherein the cartilage graft includes a micronized cartilage matrix;
   d) tensioning the flexible strand that is passed through the cartilage graft through the at least one transosseus tunnel;
   e) knotlessly fixating the cartilage graft to the bone; and
   f) applying a layer of fibrin over the cartilage graft after knotlessly fixating the cartilage graft to the bone.

2. The method as recited in claim 1, wherein the bone has vertical margins around a periphery of the cartilage defect.

3. The method as recited in claim 2, wherein the bone comprises at least a portion of the cartilage defect removed.

4. The method as recited in claim 1, further comprising drying the cartilage defect.

5. The method as recited in claim 1, wherein the at least one transosseus tunnel exits in the cartilage defect.

6. The method as recited in claim 1, wherein the at least one transosseus tunnel is three transosseus tunnels.

7. The method as recited in claim 1, comprising shuttling a free end of the flexible strand through the flexible strand to create a spliced loop around the cartilage graft.

8. The method as recited in claim 1, wherein knotlessly fixating the cartilage graft to bone is via a fixation device.

9. The method as recited in claim 8, wherein the fixation device is a screw, an anchor, a button, or a suture construct.

10. The method as recited in claim 8, wherein the fixation device is more than one fixation device.

11. The method as recited in claim 10, wherein the more than one fixation device is selected from the group consisting of a screw, an anchor, a button, a suture construct, and combinations thereof.

12. The method as recited in claim 1, wherein knotlessly fixating the cartilage graft to the bone includes:
   inserting a fixation device into the at least one transosseous tunnel at an opposite end of the at least one transosseous tunnel from the cartilage graft.

13. The method as recited in claim 1, comprising:
   drilling a second transosseus tunnel; and
   tensioning a second flexible strand that is passed through the cartilage graft and through the second transosseus tunnel,
   wherein the cartilage graft is fixated to the bone by the flexible strand and the second flexible strand.

14. The method as recited in claim 13, comprising:
   drilling a third transosseus tunnel; and
   tensioning a third flexible strand that is passed through the cartilage graft and through the third transosseus tunnel,
   wherein the cartilage graft is fixated to the bone by the flexible strand, the second flexible strand, and the third flexible strand.

15. The method as recited in claim 14, comprising:
   drilling a fourth transosseus tunnel; and
   tensioning a fourth flexible strand that is passed through the cartilage graft and through the fourth transosseus tunnel,
   wherein the cartilage graft is fixated to the bone by the flexible strand, the second flexible strand, the third flexible strand, and the fourth flexible strand,
   wherein the flexible strand is positioned in a first quadrant of the cartilage graft, the second flexible strand is positioned in a second quadrant of the cartilage graft, the third flexible strand is positioned in a third quadrant of the cartilage graft, and the fourth flexible strand is positioned in a fourth quadrant of the cartilage graft,
   wherein the first quadrant, the second quadrant, the third quadrant, and the fourth quadrant are different quadrants of the cartilage graft.

16. The method as recited in claim 1, wherein the cartilage graft includes a cartilage disk having a plurality of pores.

17. The method as recited in claim 1, wherein the cartilage defect includes an osteochondral defect or a chondral defect.

18. The method as recited in claim 1, comprising:
   after applying the fibrin, allowing the cartilage graft to sit for a predefined amount of time;
   ranging a joint associated with the bone after the predefined amount of time; and
   closing the joint.

19. The method as recited in claim 1, comprising:
   prior to passing the flexible strand through the at least two different openings of the cartilage graft, placing a template over the cartilage defect;
   marking the template to indicate a size and a shape of the cartilage defect; and
   trimming the cartilage graft down to the size and the shape indicated by the template.

20. A method for repairing a cartilage defect, comprising:
   drilling a first transosseus tunnel through a bone, wherein the first transosseus tunnel extends continuously from a first opening at a first location of the bone to a second opening at a second location of the bone;

drilling a second transosseus tunnel through the bone, wherein the second transosseus tunnel extends continuously from a third opening at a third location of the bone to a fourth opening at a fourth location of the bone;

drilling a third transosseus tunnel through the bone, wherein the third transosseus tunnel extends continuously from a fifth opening at a fifth location of the bone to a sixth opening at a sixth location of the bone;

passing a first flexible strand through a first pore and a second pore of a cartilage disk of a cartilage graft to form a first mattress stitch;

passing a second flexible strand through a third pore and a fourth pore of the cartilage disk to form a second mattress stitch;

passing a third flexible strand through a fifth pore and a sixth pore of the cartilage disk to form a third mattress stitch, wherein the first mattress stitch is positioned in a first one-third section of the cartilage disk, the second mattress stitch is poisoned in a second one-third section of the cartilage disk, and the third mattress stitch is positioned in a third one-third section of the cartilage disk;

passing the first flexible strand through the first transosseus tunnel;

passing the second flexible strand through the second transosseus tunnel;

passing the third flexible strand through the third transosseus tunnel;

tensioning the first flexible strand, the second flexible strand, and the third flexible strand to approximate the cartilage disk to the bone, wherein, once approximated, the cartilage disk is adjacent to the first opening, the third opening, and the fifth opening;

inserting a first knotless suture anchor into the second opening of the first transosseus tunnel at an opposite end of the first transosseus tunnel from the cartilage disk, thereby knotlessly fixating the first flexible strand relative to the bone;

inserting a second knotless suture anchor into the fourth opening of the second transosseus tunnel at an opposite end of the second transosseus tunnel from the cartilage disk, thereby knotlessly fixating the second flexible strand relative to the bone; and inserting a third knotless suture anchor into the sixth opening of the third transosseus tunnel at an opposite end of the third transosseus tunnel from the cartilage disk, thereby knotlessly fixating the third flexible strand relative to the bone, wherein the cartilage graft includes a micronized cartilage matrix.

\* \* \* \* \*